US012440643B1

(12) United States Patent
Shuter et al.

(10) Patent No.: US 12,440,643 B1
(45) Date of Patent: Oct. 14, 2025

(54) RELAXATION SYSTEM WITH HAPTIC ACTUATOR

(71) Applicant: Calm and Sense Technologies, LLC, Palm Beach Gardens, FL (US)

(72) Inventors: Daniel Shuter, New York, NY (US); Angela Sun, New York, NY (US); David Shuter, Palm Beach Gardens, FL (US)

(73) Assignee: CALM AND SENSE TECHNOLOGIES, LLC, Palm Beach Gardens, FL (US)

(*) Notice: Subject to any disclaimer, the term of this patent is extended or adjusted under 35 U.S.C. 154(b) by 0 days.

(21) Appl. No.: 18/930,323

(22) Filed: Oct. 29, 2024

(51) Int. Cl.

| | |
|---|---|
| ***A61M 21/02*** | (2006.01) |
| ***A61H 23/02*** | (2006.01) |
| ***A61M 21/00*** | (2006.01) |

(52) U.S. Cl.
CPC ......... *A61M 21/02* (2013.01); *A61H 23/0236* (2013.01); *A61H 2201/102* (2013.01); *A61H 2201/123* (2013.01); *A61H 2201/5005* (2013.01); *A61H 2201/5007* (2013.01); *A61M 2021/0016* (2013.01); *A61M 2021/0022* (2013.01); *A61M 2205/05* (2013.01); *A61M 2205/8206* (2013.01)

(58) Field of Classification Search
CPC .......... A61M 21/02; A61M 2021/0016; A61M 2021/0022; A61M 2205/05; A61M 2205/8206; A61H 23/0236; A61H 2201/102; A61H 2201/123; A61H 2201/5005; A61H 2201/5007
See application file for complete search history.

(56) References Cited

U.S. PATENT DOCUMENTS

| | | | | |
|---|---|---|---|---|
| 11,197,974 | B2 | 12/2021 | Kremer et al. | |
| 11,260,198 | B2 | 3/2022 | Rabin et al. | |
| 2010/0320819 | A1* | 12/2010 | Cohen | A61H 23/0236 381/104 |
| 2017/0007488 | A1* | 1/2017 | Tan | A61L 9/03 |
| 2020/0245931 | A1 | 8/2020 | Chmelik | |
| 2022/0331198 | A1* | 10/2022 | Dietrich | A61H 23/02 |
| 2022/0362095 | A1* | 11/2022 | Rabin | A61H 19/30 |
| 2023/0166071 | A1 | 6/2023 | Adriaenssen et al. | |
| 2024/0001069 | A1 | 1/2024 | Jun | |
| 2024/0001070 | A1 | 1/2024 | Jun | |
| 2024/0050689 | A1* | 2/2024 | English | A61M 21/00 |

* cited by examiner

*Primary Examiner* — Carrie R Dorna
*Assistant Examiner* — Joshua Daryl D Lannu
(74) *Attorney, Agent, or Firm* — Rankin, Hill & Clark LLP

(57) ABSTRACT

A relaxation device includes an enclosure, a linear vibrator, at least one processing device, and a power source. The linear vibrator is positioned in the enclosure and is configured to impart a uniaxial force on at least a portion of the enclosure. The processing device is in electrical communication with the linear vibrator and is configured to control operation of the linear vibrator. The power source is in the enclosure and electrically connected with the processing device and the linear vibrator.

15 Claims, 4 Drawing Sheets

RELAXATION SYSTEM WITH HAPTIC ACTUATOR

BACKGROUND

Relaxation devices have been used for various purposes, including stress relief, meditation aid, and sleep assistance. Many existing relaxation devices include vibration sources to provide a signal to a user when to inhale and exhale during a breathing exercise. In existing relaxation devices, however, power consumption of the vibration source can be relatively high as compared to the vibrations felt by the user. Moreover, the vibration source may be overly audible to the user, which can be disagreeable to some users.

SUMMARY

In view of the foregoing, a relaxation device includes an enclosure, a linear vibrator, at least one processing device, and a power source. The linear vibrator is positioned in the enclosure and is configured to impart a uniaxial force on at least a portion of the enclosure. The processing device is in electrical communication with the linear vibrator and is configured to control operation of the linear vibrator. The power source is in the enclosure and electrically connected with the processing device and the linear vibrator.

DETAILED DESCRIPTION

Figure 1:
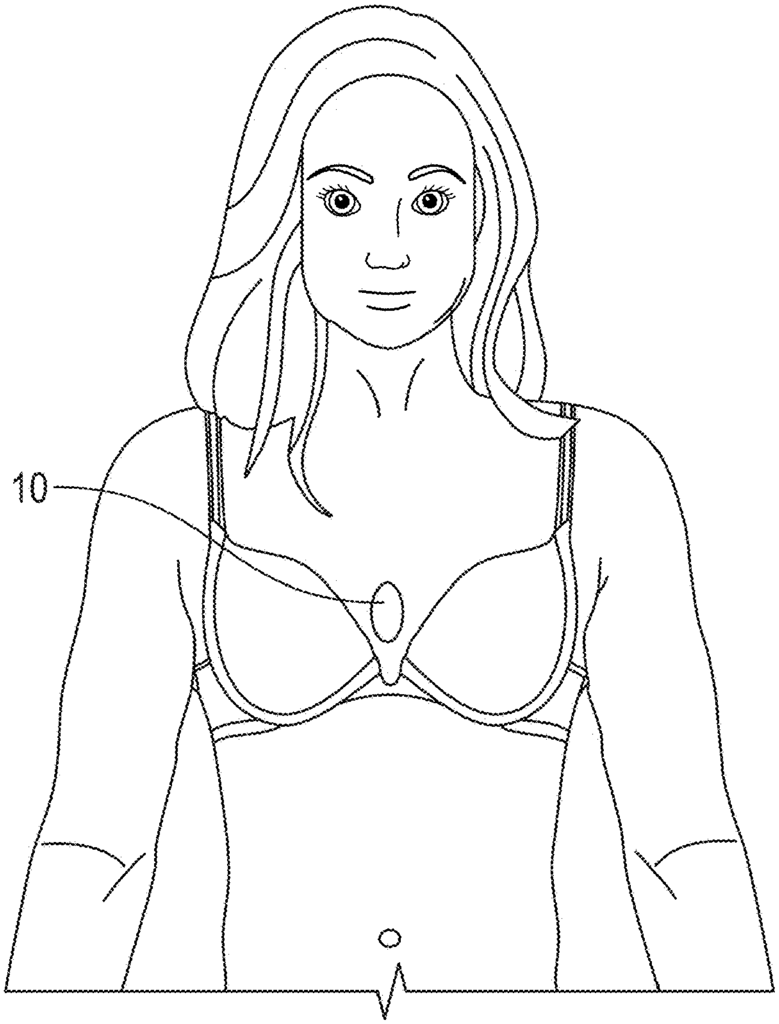
FIG. 1 is a schematic depiction of a relaxation device resting on a user's sternum.

The detailed description and specific examples, while describing particular embodiments, are intended for purposes of illustration only and are not intended to limit the scope of the invention. These embodiments and other features, aspects, and advantages will become better understood from the following description, appended claims, and accompanying drawings. The figures are merely schematic and are not drawn to scale, and the same reference numerals are used throughout the figures to indicate the same or similar parts.

FIG. 1 depicts a relaxation device 10 that is intended to rest on a person's sternum for guiding a user in paced breathing to encourage relaxation and/or sleep induction. The relaxation device 10 can also contact a person at locations other than the sternum, and could also be held in the person's hand or hands, if desired. The relaxation device 10 includes an enclosure 12 that can take the form shown in FIG. 2; however, the enclosure 12 can take other forms as well. With reference to FIG. 3, the relaxation device 10 utilizes a linear vibrator 14 to generate a uniaxial force felt by the user for relaxation purposes. The enclosure 12 houses main components of the relaxation device 10 including the linear vibrator 14, at least one processing device, which includes a processing unit 16 schematically depicted in FIG. 4, and a power source 18.

The linear vibrator 14 is mounted within the enclosure 12 and is configured to impart a uniaxial force on at least a portion of the enclosure 12. The linear vibrator 14 is designed to produce linear motion substantially along a single axis 22, as opposed to rotary vibrators, e.g., an eccentric rotating mass (ERM) motor which generates multidirectional vibrations. The relaxation device 10 may employ different types of linear vibrators including a speaker coil and a linear vibration motor. When the linear vibrator 14 is a speaker coil it operates on the same principle as an audio speaker: a voice coil is suspended in a magnetic field, and when an alternating current is applied to the coil, the coil moves back and forth within the magnetic field generating a linear motion. When the linear vibrator 14 is a linear vibration motor it typically uses a spring-mass system with an electromagnet to generate oscillations along a single axis.

The linear vibrator 14 can be designed to operate within a specific frequency range that can provide effective for haptic sensations to the user while remaining relatively quiet to user. Infrasonic sound, also known as low frequency sound, is a type of sound wave with a frequency below the human hearing range, which is generally 20 Hertz (Hz) or lower. The relaxation device 10 can be configured such that the linear vibrator 14 operates at frequencies between 45-100 Hz, which is near the infrasonic range. More specifically, the relaxation device 10 can be configured such that the linear vibrator 14 operates at frequencies of 60 or 65 Hz. The linear vibrator 14 can have a resonant frequency between 45-100 Hz. More specifically, the linear vibrator 14 can have a resonant frequency between 70-90 Hz. The resonant frequency is the natural frequency at which the linear vibrator 14 oscillates most efficiently, requiring minimal input energy to maintain vibration. The linear vibrator 14 can also have a frequency response falloff of less than 50% at +/−10 Hz from the resonant frequency. Where the linear vibrator 14 has a fairly flat response or less of a falloff, the linear vibrator 14 will still operate efficiently enough farther away from the resonant frequency. Usually, linear vibration motors lose around 90% of their efficiency outside of a +/−20 Hz range from the resonant frequency. By matching, or nearly matching, the operating frequency to the resonant frequency of the linear vibrator 14, the relaxation device 10 can maximize power consumption efficiency while providing an appropriate haptic sensation to the user and still be relatively quiet.

The linear vibrator 14 is designed to provide significant vibration force while maintaining energy efficiency and quiet operation. The linear vibrator 14 is configured to generate a root mean square acceleration of at least 0.2 $g_{rms}$. This measure of vibration intensity ensures that the device provides a noticeable haptic cue to the user while also stimulating the vagus nerve, which runs under the sternum, when the relaxation device 10 is resting on the user's sternum. The linear vibrator 14 can be configured to achieve the aforementioned acceleration for every 200 mW of power consumed. This high efficiency allows for extended operation times and makes the device suitable for portable, battery-powered use.

The linear vibrator 14 and the enclosure 12 are designed and the linear vibrator 14 is mounted within the enclosure 12 to optimize the use of space. The longest dimension (length L) of the enclosure 12 can be 60.00 mm, and the widest dimension (width W) of the enclosure 12 can be 51.60 mm.

Figure 5:
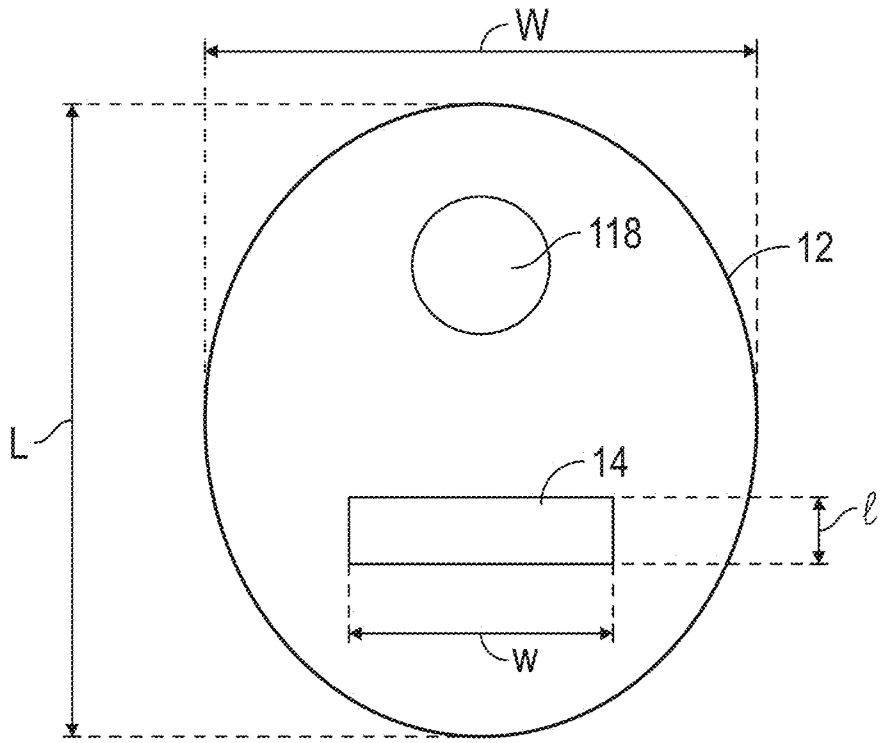
FIG. 5 is a schematic depiction of a cross section taken along line 5-5 in FIG. 4.

As such, the relaxation device can be compact allowing it to comfortably rest on a person's sternum, or elsewhere, and can also be easily held in a person's hand. Along a cross section taken normal to the single axis 22 (FIG. 3) and along the longest dimension of the enclosure 12, an area occupied by the linear vibrator is about 5% an overall internal area of the enclosure 12 through this cross section. For example, through the cross section shown in FIG. 5, the length/of the linear vibrator is 6.23 mm and the width w is 24.95 mm. The area occupied by the linear vibrator could be increased so that the area occupied by the linear vibrator could be up to about 20% an overall internal area of the enclosure 12 through the cross section shown in FIG. 5. However, occupying up to about 20% an overall internal area of the enclosure 12 through this cross section allows a relatively powerful and quiet linear vibrator 14 to be housed in a compact enclosure 12 while providing space for other components.

Figure 4:
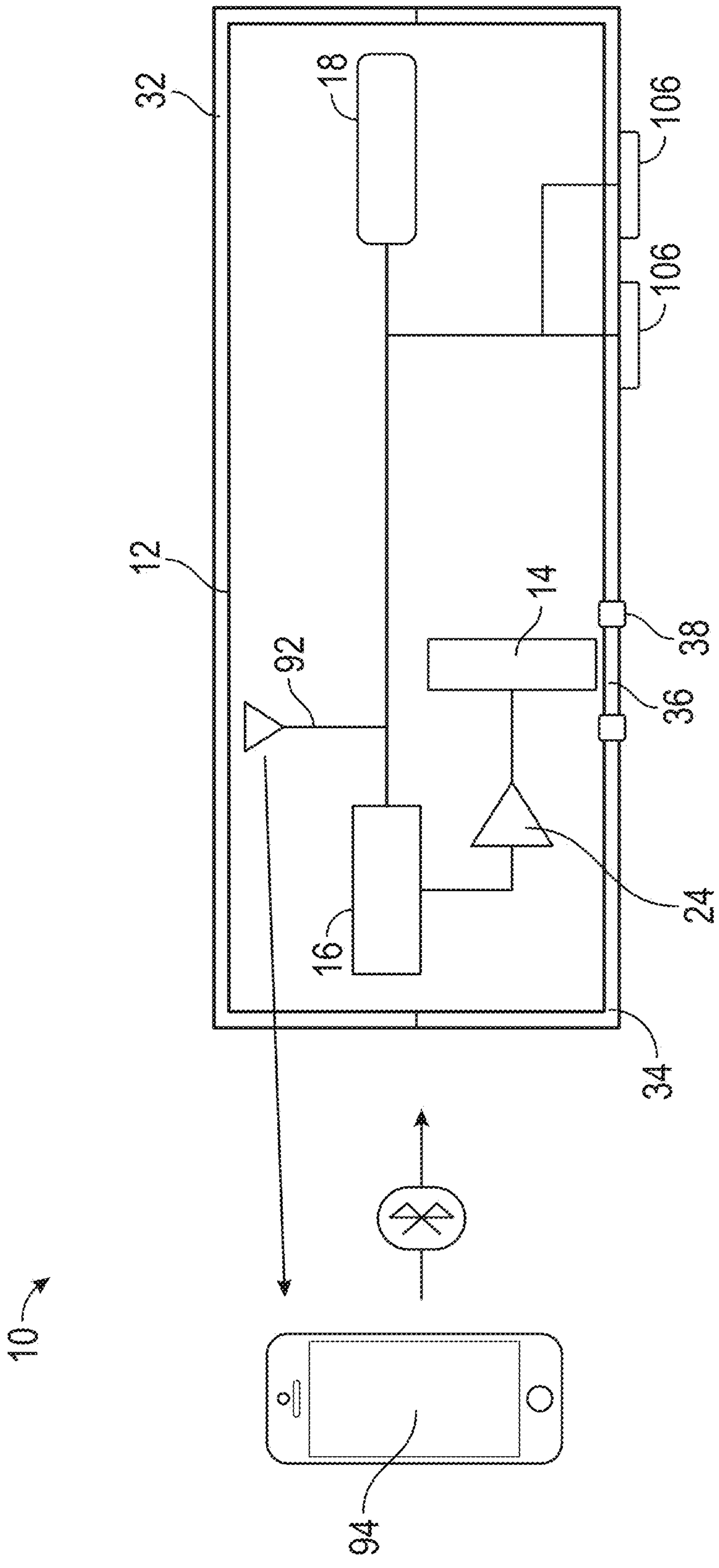
FIG. 4 is a schematic depiction of a relaxation system including the relaxation device.

The operation of the linear vibrator 14 is controlled by the at least one processing device, which can includes the processing unit 16 positioned within the enclosure. The at least one processing device can generate a sine wave signal to drive the linear vibrator 14. The amplitude of the sine wave can be varied over time, allowing for dynamic vibration patterns, e.g., to create pulsing effects or gradually increase or decrease the intensity of the vibration. With reference to FIG. 4, an amplifier 24 may be used to boost the sine wave signal before it reaches the linear vibrator 14. The amplifier 24 could be an audio amplifier or an operational amplifier, with either fixed or adjustable gain. The use of an amplifier 24 allows the device to achieve higher vibration intensities when desired.

The enclosure 12 of the relaxation device 10 houses internal components and effectively transmits the vibrations to the user. The enclosure 12 may be designed in various shapes, such as spherical, cylindrical, or ergonomically contoured to fit comfortably on a user's sternum or against different parts of the body. The specific shape chosen can optimize both the transmission of vibrations and user comfort. The enclosure 12 can constructed from materials that balance durability, vibration transmission, and user comfort. Such materials include rigid plastics, e.g., acrylonitrile butadiene styrene (ABS), polycarbonate, and/or metals.

Figure 2:
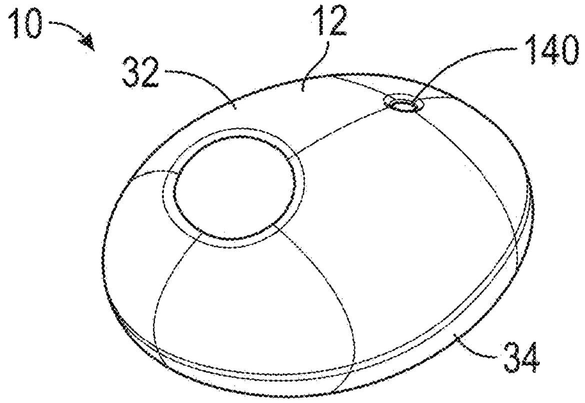
FIG. 2 is a perspective view of an example of the relaxation device of FIG. 1.
Figure 3:
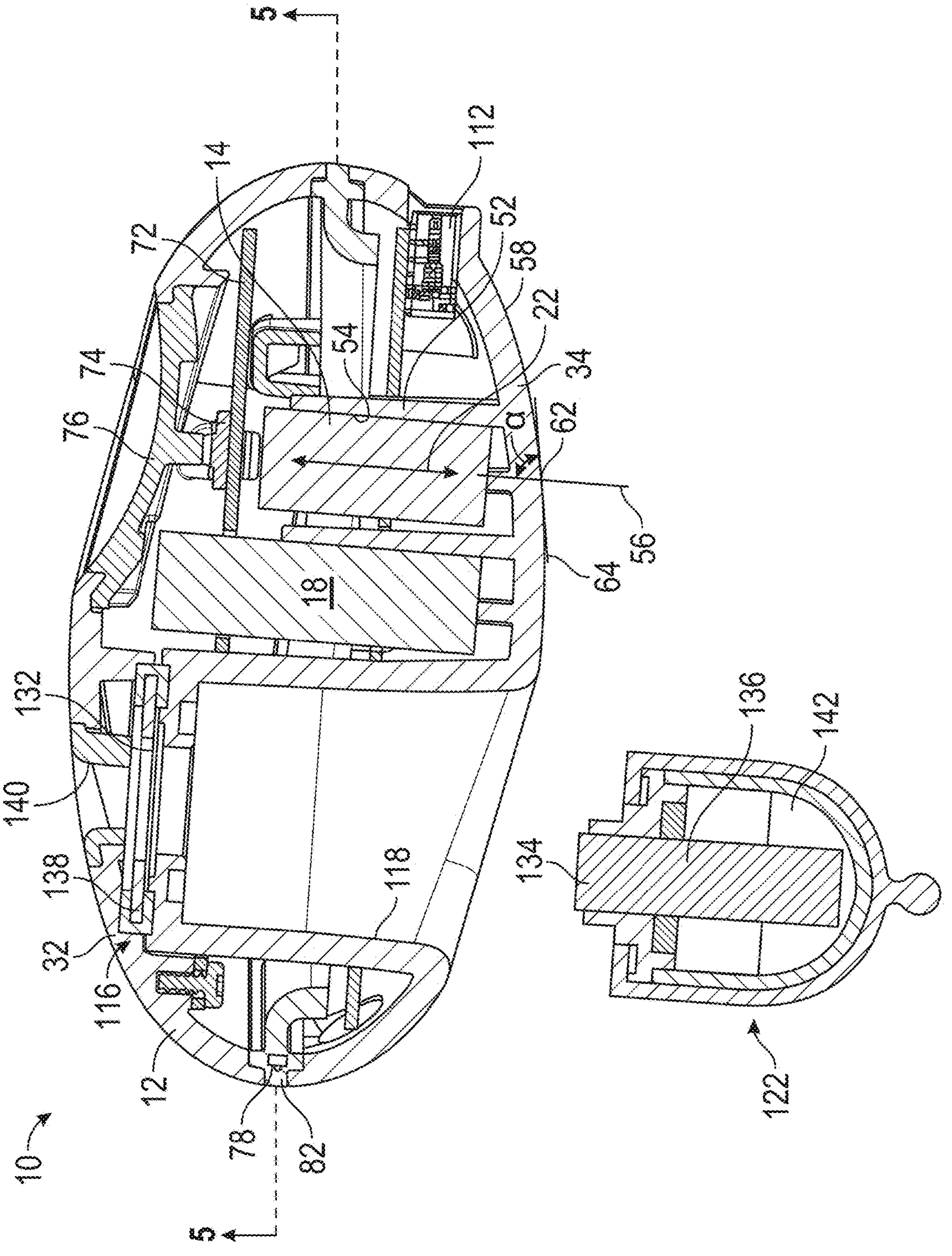
FIG. 3 a cross-sectional view of the relaxation device, showing the arrangement of a linear vibrator, processing device, and power source within an enclosure.

With reference to FIGS. 2 and 3, the enclosure 12 can include an upper shell 32 connected to a lower shell 34 via conventional fastening methods including fasteners, adhesives, welding and the like. If desired, and schematically depicted in FIG. 4, the enclosure 12 can include a movable outer wall portion 36 that is directly influenced by the linear vibrator 14. In some embodiments, the linear vibrator 14 can be directly connected to the movable outer wall portion 36. This allows the vibration to be directly transferred to the surface that comes into contact with the user. The movable outer wall portion 36 can be connected to a relatively fixed outer wall portion, which in the embodiment illustrated in FIG. 4 is the lower shell 34, via a resilient ring 38. This resilient ring 38 allows for controlled movement of the movable outer wall portion 36 with respect to the relatively fixed outer wall portion, e.g., the lower shell 34, while maintaining the integrity of the enclosure 12 and preventing ingress of dust or moisture into the interior of the enclosure 12. The movable outer wall portion 36 may be made of a slightly more flexible material than the fixed outer wall portion to enhance vibration transmission. The size and shape of the movable outer wall portion 36 can be optimized to provide an effective contact area for the user while maintaining the desired vibration characteristics. When the linear vibrator 14 imparts the uniaxial force, the movable outer wall portion 36 moves relative to the fixed outer wall portion. This movement is typically very small (in the range of micrometers to a few millimeters) while being sufficient to create the desired haptic effect. The linear vibrator 14 can impart a root mean square acceleration of at least 0.2 $g_{rms}$ on the movable outer wall portion 36.

With reference to FIG. 3, a vibrator mounting post 52 is positioned within and connected to the enclosure 12. The vibrator mounting post 52 can be integrally formed with the lower shell 34, although the vibrator mounting post 52 can be connected with the enclosure 12 in other manners. The vibrator mounting post 52 defines a mounting surface 54, which can be parallel to the direction of the uniaxial force and the single axis 22. The linear vibrator 14 mounts to the mounting surface 54, e.g., via an adhesive, to align the linear vibrator 14 to produce linear motion substantially along the single axis 22. This design helps to direct and focus the vibration force.

The geometry of the enclosure 12 can be designed so that a line collinear with the uniaxial force, e.g. a linear extension 56 of the single axis 22, intersects an outer surface 58 of the enclosure 12 at a point 62. The outer surface 58 including the point 62 is intended to rest on the user's sternum (see FIG. 1) when the relaxation device is in use. A tangent line 64 tangent to the outer surface 58 at the point 62 forms an angle α of at least 80 degrees with the linear extension 56 of the single axis 22. The choice of the linear vibrator 14 and the near-perpendicular orientation leverages the frequency of vibration at or nearly outside of human hearing to deliver a nearly silent but powerful haptic indication. To fully benefit from the force generated by the linear vibrator 14, it is mounted so its uniaxial force is into the body. Additionally, the linear vibrator 14 is mounted in a way that does not dampen its vibration. To achieve this, the linear vibrator 14 is mounted without foam or another elastic material. Finally, if the entire enclosure 12 is meant to vibrate, all joints, fasteners, and component connections are vibration resistant.

The at least one processing device, which can include the processing unit 16 in FIG. 4, is in in electrical communication with and controls the operation of the linear vibrator 14 as well as manages various other functions of the relaxation device 10. The at least one processing device can include a microcontroller unit (MCU), which is not visible in FIG. 3, mounted to a circuit board 72. The at least one processing device can include both program memory (e.g., Flash) for storing firmware and random access memory (RAM) for runtime operations. The at least one processing device can further include a digital-to-analog converter to generate the analog sine wave signal described above to drive the linear vibrator 14.

The at least one processing device can also include input/output (I/O) interfaces such as a switch 74 mounted to the circuit board 72 for interfacing with a control button 76 (or touch sensors). The I/O interfaces that are part of the at least one processing device can also be provided to control LEDs 78 (only one depicted in FIG. 3) that can be mounted in a light ring 82 positioned between the upper shell 32 and the lower shell 34. The I/O interfaces that are part of the at least one processing device can also interface with a power management system for the power source 18. With reference to FIG. 4, wireless communication modules 92 (e.g., Bluetooth Low Energy) can be provided as part of the at least one processing device to provide communication between a smart phone 94. In such an instance, the processor on the smart phone 94 can form a component of the at least one processing device and the smart phone 94 and any connected application running on the smart phone 94 in combination with the relaxation device 10 can make up a relaxation system.

In some implementations, the at least one processing device may receive feedback from the linear vibrator 14 (e.g., through back-EMF measurement or dedicated position sensors) to monitor its actual motion. Based on the feedback and desired vibration pattern, the at least one processing device can make real-time adjustments to the driving signal to maintain the desired vibration characteristics.

The at least one processing device can interface with electrodes 106, which can be dry ECG (electrocardiogram) biopotential electrodes that do not require the typical electrolytic conductive gel and skin preparation as compared to wet electrodes. At least two, and perhaps more, electrodes 106 can be mounted to the enclosure 12 and in electrical communication with the processing unit 16. The electrodes 106 are mounted to the enclosure 12 in a manner such that when the enclosure 12 is placed on the user's sternum (see FIG. 1) ionic currents from the user's body surface are converted into electrical signals for later processing by the at least one processing device, which can be useful to adaptively adjust the vibration patterns.

The relaxation device 10 includes user interface elements such as the control button 76, or similar touch-sensitive area integrated into the enclosure 12, to control power delivery, intensity control, and/or mode selection. The LED lights 78 may be incorporated to show power status, battery level, or current operation mode. A charging port 112 is provided in the enclosure 12 for charging the relaxation device 10. The is charging port 112 is in electrical communication with the processing unit 16 and the power source 18, which can be a rechargeable battery.

If desired, the relaxation device 10 can include scent release mechanism 116, which is mounted within the enclosure 12. As detailed in FIG. 3, the enclosure 12 defines a scent capsule cavity 118 and a replaceable scent capsule 122 is receivable in the scent capsule cavity 118 and operably connectable with the scent release mechanism 116. The scent release mechanism 116 can include a disk 132 with a plurality of apertures (not visible in FIG. 3). When the scent capsule 124 is properly inserted, a free end 134 of a capillary wick 136 contacts the disk 132. A piezoelectric atomizer 138 is connected to the disk 132. When energized under the control of the at least one processing device to which it is electrically connected, the piezoelectric atomizer 138 vibrates the disk 132, drawing scent solution 142 in the replaceable scent capsule 122 from the capillary wick 136 and atomizing it as it passes through the apertures in the disk 132. The atomized scent solution then exits the relaxation device 10 through a scent outlet 140 provided in the enclosure 12.

As discussed above, the linear vibrator 14 and the enclosure 12 are designed and the linear vibrator 14 is mounted within the enclosure 12 to optimize the use of space. As such, by providing the linear vibrator 14 with a relatively small cross-sectional area as compared to the cross-sectional area of the enclosure 12 (see FIG. 5), the enclosure 12 can define the scent capsule cavity 118 configured to receive the replaceable scent capsule 124. Such a design allows for the relaxation device 10 to include more features. And, in the cross section taken normal to the single axis 22 (FIG. 3) and along the longest dimension L of the enclosure 12, the area occupied by the linear vibrator 14 is less than 20% an overall internal area of the enclosure 12 through this cross section.

It will be appreciated that various of the above-disclosed embodiments and other features and functions, or alternatives or varieties thereof, may be desirably combined into many other different systems or applications. Also that various presently unforeseen or unanticipated alternatives, modifications, variations or improvements therein may be subsequently made by those skilled in the art which are also intended to be encompassed by the following claims.

The invention claimed is:

1. A relaxation device comprising:

an enclosure configured to rest on a person's sternum or be held in a person's hand, the enclosure including an upper shell and a lower shell made from a rigid plastic or metal;

a linear vibrator mounted in the enclosure and positioned within the enclosure to impart a uniaxial force on a portion of the lower shell made from the rigid plastic or metal to provide a haptic sensation, wherein the linear vibrator has a root mean square acceleration of at least 0.2 $g_{rms}$ for every 200 mW of power consumed by the linear vibrator;

at least one processing device in electrical communication with the linear vibrator, the at least one processing device being configured to control operation of the linear vibrator; and a power source in the enclosure and electrically connected with the at least one processing device and the linear vibrator.

2. The relaxation device of claim 1, wherein the linear vibrator has a resonant frequency between 45-100 Hz.

3. The relaxation device of claim 2, wherein the linear vibrator has an operating frequency between 45-100 Hz.

4. The relaxation device of claim 3, wherein the linear vibrator has an operating frequency of 60 Hz or 65 Hz.

5. The relaxation device of claim 1, wherein the linear vibrator is a speaker coil.

6. The relaxation device of claim 1, wherein the linear vibrator is a linear vibration motor including a spring-mass system with an electromagnet.

7. The relaxation device of claim 6, wherein along a cross section taken normal to an axis parallel to the uniaxial force and along a longest dimension of the enclosure, an area occupied by the linear vibrator is rectangular and less than 20% an overall internal area of the enclosure through the cross section.

8. The relaxation device of claim 7, wherein the linear vibrator is rectangular in shape along a cross section taken parallel to the uniaxial force.

9. The relaxation device of claim 1, wherein the at least one processing device generates a sine wave signal to drive the linear vibrator.

10. The relaxation device of claim 9, wherein the sine wave signal varies in amplitude over time.

11. The relaxation device of claim 9, further comprising an amplifier in electrical communication with the at least one processing device and the linear vibrator, wherein the amplifier amplifies the sine wave signal.

12. The relaxation device of claim 11, wherein the amplifier is an audio or operational amplifier.

13. The relaxation device of claim 12, wherein the amplifier has either fixed or adjustable gain.

14. A relaxation device comprising:

an enclosure configured to rest on a person's sternum or be held in a person's hand, the enclosure including an upper shell and a lower shell made from a rigid plastic or metal;

a linear vibrator mounted in the enclosure and positioned within the enclosure to impart a uniaxial force on a portion of the lower shell made from the rigid plastic or metal to provide a haptic sensation;

at least one processing device in electrical communication with the linear vibrator the at least one processing device being configured to control operation of the linear vibrator;

a power source in the enclosure and electrically connected with the at least one processing device and the linear vibrator; and a vibrator mounting post positioned within and integrally formed with the lower shell, the vibrator mounting post defining a mounting surface parallel to a direction of the uniaxial force, wherein the vibrator mounts to the mounting surface.

15. The relaxation device of claim 14, wherein the enclosure defines a scent capsule cavity configured to receive a replaceable scent capsule, and wherein along a cross section taken parallel to the uniaxial force and along a longest dimension of the enclosure, the power source is positioned between the scent capsule cavity and the linear vibrator.

* * * * *